(12) United States Patent
Dick et al.

(10) Patent No.: US 7,879,809 B2
(45) Date of Patent: Feb. 1, 2011

(54) FISH PRODUCTION

(75) Inventors: Clayton Paul Dick, Guelph (CA); Daniel Earl Snyder, Indianapolis, IN (US); Joseph Raymond Winkle, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 477 days.

(21) Appl. No.: 11/912,435

(22) PCT Filed: May 15, 2006

(86) PCT No.: PCT/US2006/018797

§ 371 (c)(1), (2), (4) Date: Oct. 24, 2007

(87) PCT Pub. No.: WO2006/127322

PCT Pub. Date: Nov. 30, 2006

(65) Prior Publication Data

US 2008/0188427 A1 Aug. 7, 2008

Related U.S. Application Data

(60) Provisional application No. 60/684,886, filed on May 26, 2005.

(51) Int. Cl.
  A61K 31/7034 (2006.01)
  A61K 31/704 (2006.01)
  A01N 43/22 (2006.01)
  A01N 45/02 (2006.01)
  C07H 17/08 (2006.01)
  C07H 7/04 (2006.01)

(52) U.S. Cl. ............................. 514/28; 514/31; 536/6.5; 536/7.1

(58) Field of Classification Search ....................... None
See application file for complete search history.

(56) References Cited

U.S. PATENT DOCUMENTS

| 5,571,901 A | 11/1996 | Boeck et al. |
| 6,455,504 B1 | 9/2002 | Lewer et al. |
| 6,664,237 B1 * | 12/2003 | Snyder ........................ 514/28 |
| 7,312,200 B2 * | 12/2007 | Malsam et al. ................ 514/28 |
| 2006/0141009 A1 * | 6/2006 | Huron et al. ................ 424/442 |

FOREIGN PATENT DOCUMENTS

| WO | WO 00/60952 | 10/2000 |
| WO | WO 01/11963 | 2/2001 |
| WO | WO 01/70027 | 9/2001 |
| WO | WO 2004/014143 | 2/2004 |
| WO | WO 2004/065402 | 8/2004 |

OTHER PUBLICATIONS

Meyer et al., "Aquaculture Disease and Health Management" Journal of Animal Science (1991) vol. 69 No. 10, pp. 4201-4208.*
Cleveland et al., "An ecological risk assessment for spinosad use on cotton" Pest Management Science (2001) vol. 58 pp. 70-84.*
Stone, J., et al., "The efficacy of emamectin benzoate as an oral treatment of sea lice, lepeophtheirus salmonis (Kroyer), infestations in Atlantic Salmon, Salmo Salar L," *Journal of Fish Diseases*, 22(4):261-270 (Jul. 1999).
CDS Tomlin (ed.), "The Pesticide Manual (12th) Edition", British Crop Protection Council, Entry 284, pp. 840-842 (2000).
CDS Tomlin (ed.), "The Pesticide Manual (12th Edition)," The British Crop Protection Council, Entry 702, pp. 840-842.

* cited by examiner

Primary Examiner—Eric S Olson
(74) Attorney, Agent, or Firm—James J. Sales

(57) ABSTRACT

This invention is directed to the use of spinosyn or a physiologically acceptable derivative or salt thereof for improved production of fish; controlling ectoparasite infestations in aquaculture raised fish; and fish feed formulations.

16 Claims, No Drawings

FISH PRODUCTION

This application claims priority of PCT/US06/18797 filed May 15, 2006, which claims priority to US provisional application 60/684,886 filed May 26, 2005, both of which are herein incorporated by reference for all purposes.

BACKGROUND OF THE INVENTION

Extensive fishing of natural waters has lead to a reduction in fish numbers. It is now recognized that fishing at a rate to sustain natural populations will not provide the world's needs for fish as a food. This has lead to the development of the aquaculture industry, in which fish and other aquatic species are produced in a controlled environment within bodies of water. These fish farms can be established in ocean or fresh water depending on the type and normal environment of the fish. Fish is, worldwide, the single biggest source of protein, and aquaculture is therefore an increasingly important means of producing food. Furthermore, since the fish are in a controlled environment, means are being sought to control disease and maximize production.

Parasites, causing little apparent damage in feral fish populations, may cause diseases of great importance in farmed fish, leading to pathological changes, decrease of fitness or reduction of the market value of fish. Despite considerable progress in fish parasitology, major gaps still exist in the knowledge and control of fish parasites. Control of many important parasitic diseases are still far from satisfactory and further options are needed.

Development of aquaculture during the last decades has resulted in much greater attention being paid to problems posed by parasites and their importance to growth rate, feed efficiency and body weight leading to constraints in the advancement and productivity of aquaculture. Besides direct losses caused by mortality, parasites may have considerable impact on growth and behavior of fish, their resistance to other stressing factors, susceptibility to predation, etc.; their presence may also reduce marketability of fish.

Parasitic crustaceans are important pathogens and diseases caused by them may result in considerable economic losses. The most important group among parasitic crustaceans are undoubtedly sea lice.

Sea lice is the term used to describe several species of ectoparasitic copepods (a type of crustacean) of the genera *Lepeophtheirus* and *Caligus* that parasitize cultured fish and may cause diseases with damage to the epidermis and in severe cases death through osmoregulatory failure or secondary infections. *Lepeophtheirus salmonis* is now recognized as one of the most serious pathogens of marine farmed Atlantic salmon. This species and *Caligus elongatus* have economic impact on farmed salmonids in the northern hemisphere. Other caligids pathogenic to cultured or wild fish are *C. patulus, C curtus, C. clemensi, C. rogercressey; C teres, C. orientalis, C. epidemicus* and *Pseudocaligus apodus*.

The most common adult copepod parasites of freshwater fishes are *Lernaea cyprinacea, Ergasilus sieboldi* (and related species), *Salmincola californiensis, S. edwardsii, Achtheres percarum, Tracheliastes maculates*, and *Caligus lacustris*. In addition, copepodids of *Lernaea* and chalimus larvae of *Achtheres* and *Salmincola* attach to gill filaments and cause epithelial hyperplasia and may be indirectly responsible for fish-kills. Copepods are also intermediate hosts for important fish parasites, including tapeworms and nematodes. Damage from these parasites may lead to fish mortalities or reduce the market value of the fish products. Finally, copepods serve as intermediate hosts for parasites that infect humans and can serve as vectors of serious human diseases like cholera.

Additional parasites of freshwater fish include monogenean trematodes (flukes or flatworms); Protozoan parasites such as *Piscinoodinium pillulare*; and *Henneguya* spp.

Formaldehyde, malathion and natural compounds show either poor efficacy or unsuitable therapeutic margins. Pyrethroids are at present the most used therapeutic against ectoparasitic copepods. Diflubenzuron and teflubenzuron added to feed are also used in significant amounts. Carbaryl and diflubenzuron are efficacious but the compounds make them unsuitable due to undesirable environmental toxicological characteristics. Emamectin benzoate belongs to the same family of drugs as ivermectin, the avermectins. It is administered in the feed and is said to be effective against all stages of sea lice reproduction. There is increasing evidence that emamectin benzoate may harm non-target animals. Despite these problems, chemotherapy remains an important component of control strategies.

The present invention provides a new technique for ectoparasitic copepod control and improved fish production.

BRIEF SUMMARY OF THE INVENTION

The present invention is directed to a method for controlling ectoparasitic infestations in aquaculture raised fish, comprising administering an effective amount of at least one spinosyn or a physiologically acceptable derivative or salt thereof to aquaculture raised fish.

The present invention is also directed toward fish feed formulations comprising 1 to 2500 mg of a spinosyn or a physiologically acceptable derivative or salt thereof in association with and per kg of a fish feed composition.

Fermentation product A83543, also known as spinosyn, includes a family of related compounds (spinosyns) produced by *Saccharopolyspora spinosa*. These are naturally derived fermentation products with a positive safety profile in contrast to currently used synthetic organically derived compounds (such as synthetic pyrethroids, organophosphates, organochlorines and carbamates), and have previously been shown to exhibit excellent insecticidal activity. Accordingly by the term "A83543 compounds" which has the same scope as the phrase "spinosyn or a physiologically acceptable derivative or salt thereof" is meant components consisting of a 5,6,5-tricyclic ring system, fused to a 12-membered macrocyclic lactone, a neutral sugar (2N,3N,4N-tri-O-methylrhamnose) and an amino sugar (forosamine). The family of natural components of A83543 include a genus taught in EPO patent application No. 0375316 and having the following general formula:

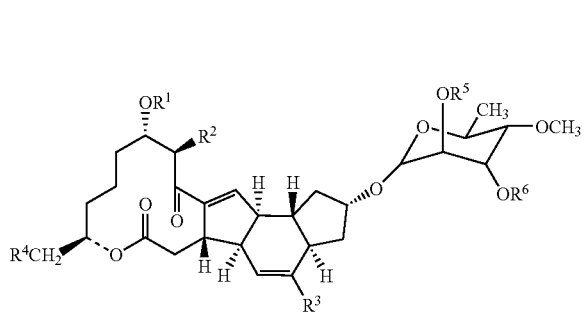

Wherein $R^1$ is H or a group selected from

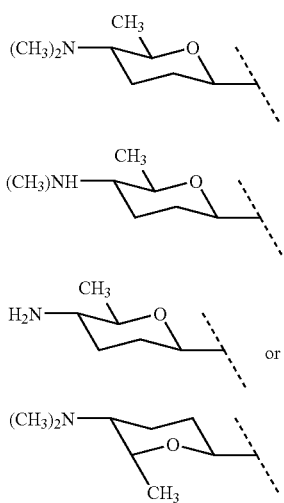

And $R^2$, $R^4$, $R^3$, $R^5$ and $R^6$ are hydrogen or methyl; or an acid addition salt thereof when $R^1$ is other than hydrogen.

The family of compounds from A83543 fermentation product has been shown to comprise individual compounds A83543A, A83453B, A83543C, A83453D, A83543E, A83453F, A83543G, A83453H, A83543J, A83453L, A83543M, A83453N, A83543Q, A83453R, A83543S, A83453T, A83453U, A83543V, A83453W, A83453Y. Boeck, et al. described spinosyns A-H and J and salts thereof in U.S. Pat. Nos. 5,362,634, 5,496,932 and 5,571,901. Mynderse, et al. described spinosyns L-N, their N-demethyl derivatives and salts thereof in U.S. Pat. No. 5,202,242. Turner, et al. described spinosyns Q-T, their N-demethyl derivatives and salts thereof in U.S. Pat. Nos. 5,591,606, 5,631,155 and 5,767,253. Spinosyns K, O, P, U, V, W and Y are described in the article by DeAmicis, C.V., et al. in American Chemical Society's Symposium Series: Phytochemicals for Pest Control (1997), Chapter 11 "Physical and Biological Properties of Spinosyns: Novel Macrolide Pest-Control Agents from Fermentation" pp. 146-154. In U.S. Pat. No. 6,001,981, various synthetic derivatives of spinosyns are described, and U.S. Pat. No. 6,455,504, wherein various spinosyn analogs are described, which are both incorporated by reference herein. Details regarding the fermentation and isolation of the spinosyns and procedures for preparing synthetic derivatives are provided in these references.

Spinosyn A (A83543A) was the first spinosyn isolated and identified from the fermentation broth of *Saccharapolyspora spinosa*. Subsequent examination of the fermentation broth revealed that the parent strain of *S. spinosa* produced a number of spinosyns (A83543A to J). Compared to spinosyn A, spinosyns B to J are characterized by differences in the substitution patterns on the amino group of the forosamine, at selected sites on the ring system and on the neutral sugar. The strains of *S. spinosa* produce a mixture of spinosyns which primary components are spinosyn A (~85%) and spinosyn D (~15%). These are the two spinosyns that are currently known as the most active as insecticides.

It is further noted that for the purposes of the present application, the term "spinosyn or a physiologically acceptable derivative or salt thereof" is defined to include an individual spinosyn factor (A83543A-H, J-W or Y) an N-demethyl or other derivative of an individual spinosyn factor, or salt thereof, or a combination thereof, consistent with the disclosure of the abovementioned references. As stated above, the term "A83543 compound" is used herein to mean an individual spinosyn factor, a derivative or salt thereof, or a combination thereof.

Each of the U.S. Patent and EP patent application describe various formulation types, parasiticidal activity and administration options in animals and agriculture for the spinosyns and physiologically acceptable derivatives or salts thereof.

As stated above, spinosad (spinosyn A and spinosyn D, as approximately a 85:15 mixture) formulations are commercially available from Dow AgroSciences, 9330 Zionsville Road, Indianapolis, Ind. 46268-1054, U.S.A., and Elanco Animal Health, a Division of Eli Lilly and Company, P.O. Box 708, 2001 W. Main Street, Greenfield, Ind. 46140, U.S.A. In addition, *S. spinosa* and mutant strains have been deposited in the Agricultural Research Service Patent Culture Collection (NRRL) National Center for Agricultural Utilization Research, ARS, USDA, 1815 North University Street, Peoria, Ill., 61604, U.S.A. (NRRL 18395, 18537, 18538, 18539, 18719, 18720, 18743, 18823 and 30141 (U.S. Pat. No. 6,455,504).

In the process of evaluating spinosad for use on crops, certain toxicity effects of spinosad were assessed in specific fish and aquatic organisms. The methodologies are as a consequence of offsite drift of spray during application to crops and through runoff from treated crop areas during and after rainstorms into a standard waterbody at the edge of the treated area. These toxicity effects on the fish and aquatic organisms assumes a concentration in water and was said to demonstrate minimal risk in aquatic species would result from the use of spinosad in crops.

The spinosyns can react to form salts. Salts that are physiologically acceptable are also useful in the methods of this invention. The salts are prepared using standard procedures for salt preparation. For example, spinosyn A can be neutralized with an appropriate acid to form an acid additional salt. The acid addition salts of spinosyns are particularly useful. Representative suitable acid addition salts include salts formed by reaction with either an organic or inorganic acid such as, for example, sulfuric, hydrochloric, phosphoric, acetic, succinic, citric, lactic, maleic, fumaric, cholic, pamoic, mucic, glutamic, camphoric, glutaric, glycolic, phthalic, tartaric, formic, lauric, stearic, salicylic, methanesulfonic, benzenesulfonic, sorbic, picric, benzoic, cinnamic and like acids.

All ratios, percentages, and parts discussed herein are "by weight" unless otherwise specified.

The term "controlling or eradicating" is used to refer to a decrease in the number of living ectoparasitic copepods at all parasitic stages (adult, pre-adult and chalimus) or other ectoparasites. The extent of reduction somewhat depends on the application rate and the active used.

The term "effective amount" also used herein means the amount which is sufficient to cause a measurable reduction in the treated ectoparasite population.

The use of spinosyn or a physiologically acceptable derivative or salt thereof in fish production leads to numerous improvements, though not all such improvements will be obtained in every embodiment of the invention. In many instances, the practice of the present invention results in an improved growth rate, improved feed efficiency, improved quality meat, improved weight gain and improved body weight. The practice of the invention can also lead to improved flavor or texture, and other benefits.

By "fish" is meant any member of the Phylum Chordata, Sub Phylum Vertebrata, and Super Class Pisces. The present invention can be practiced with any of the considerable variety of fish species.

Representative species include the following:
  Catfish
    Channel Catfish (*Ictalurus punctatus*)
    Black Bullhead (*Ictalurus melas*)
    Yellow Bullhead (*Ictalurus natalis*)
    Brown Bullhead (*Ictalurus nebulosus*)
  Carp (*Cyprinus carpio*)
  Crucian Carp (*Carassius carassius*)
  Trout
    Rainbow (formerly called Salmo gairdneri, now called *Oncorhynchus mykiss*)
    Brown (*Salmo trutta*)
    Speckled brook (*Salvelinus fontinalis*)
  Salmon
    Atlantic (*Salmo salar*)
    Coho (*Oncorhynchus kisutch*)
    Chinook or King Salmon (*Onorhynchus tshawytscha*)
  Tench (*Tinca tinca*)
  Roach (*Rutilus rutilus*)
  Pike (*Esox lucius*)
  Pike-Perch (*Lucioperca lucioperca*)
  Dover Sole
  Turbot
  Yellowtail (*Seriola quinqueradiata*)
  Bass
    Smallmouth (*Micropterus dolomieui*)
    Largemouth (*Micropterus salmoides*)
    Striped (*Morone saxatilis*)
  Milkfish (*Chanos chanos*)
  Tilapia (*Sarotherodon* sp.)
  Tilapia (*Tilapia* sp.)
  Gray Mullet (*Mugil cephalus*)
  Eels
    American (*Anguilla rostrata*)
    European (*Anguilla anguilla*)
    Japanese (*Anguilla japonicus*)
  Cod
    Atlantic cod (*Gadus morhua*)

Other species with which the present invention can be practiced will be apparent to those skilled in the art.

In aquaculture, a practical mode of delivering a substance is in the feed. Indeed, fish feeds are a standard article of commerce, often tailored for an individual species. Typically, the feed is in the form of powder, particles, crumbles and pellets depending on the particular fish species, stage of development and other factors known to those skilled in the art. Therefore, in practicing the present invention, while other routes of delivery can be employed, the preferred method of delivery is in or on a fish feed and preferably a nutritionally balanced fish feed. The spinosyn or physiologically acceptable derivative or salt is dispersed in or top-dressed onto the fish feed by known techniques.

The term feed is generally used to describe a product which meets the daily nutritional needs of the fish being fed with it, ie. It contains all the essential nutrients. The term "feedstuff" in comparison is used to refer to a component of the complete feed, such as protein or fish oil or a component containing the necessary proteins and oils but without the proper vitamin or mineral content. The term nutritionally balanced or complete includes both complete feeds and feedstuffs.

Although frequently termed fish oil, a more accurate term is perhaps lipid and both terms are used interchangeably.

Formulations of the present invention may comprise or may be used in the preparation of a liquid or dry concentrate formulation referred to as a Type A medicated article as defined in the United States Code of Federal Regulations, Title 21, Section 558, incorporated herein by reference. As is known by those skilled in the art, a Type A medicated article may be used in the preparation of another Type A medicated article or a Type B or Type C medicated feed, both Type B and Type C are as defined in the United States Code of Federal Regulations, Title 21, Section 558. In Type A medicated articles, the active agent(s) are at a concentration higher than suitable for direct administration and require dilution to said direct administration amounts. Similarly, a Type B medicated feed may be used in the preparation of another Type B medicated feed or a Type C medicated feed. A Type B medicated feed is prepared by diluting a Type A medicated article or another Type B medicated feed. A Type C medicated feed is suitable for direct administration without the need for further mixing or dilution.

Generally, liquid Type A medicated articles can be mixed into either liquid or dry supplements or into final feeds. A concentrated liquid Type A medicated article or liquid Type B medicated feed may be applied to dry feeds through a dribble bar in the mixer, by spraying onto the feed while mixing, or by other techniques known to those skilled in the art. It is believed the liquid concentrate may be mixed into liquid feed supplements or sprayed onto dry feeds or dispensed by conventional machines designed to accommodate liquid formulations.

Type B medicated feed may be liquid or dry and is intermediate between a Type A medicated article and a Type C medicated feed, which is a complete feed to be fed directly to fish. The Type B formulation contains a substantial quantity of nutrients, including vitamins and/or minerals and/or other nutritional ingredients in an amount not less than 25% by weight of the formulation. The amount of Category I pharmacologically active agent in Type B medicated feeds cannot exceed 200 times the maximum daily use level in a final feed or Type C medicated feed. Category I is the designation used by the United States Code of Federal Regulations for those active agents, for which no withdrawal period is required at the lowest use level in each species for which they are approved.

The composition of Type B medicated feeds varies from physiologically acceptable diluents to conventional concentrates designed to provide protein, vitamins, minerals, amino acids, or other nutritive ingredients. Type B medicated feeds may be a simple mix of a drug with suitable diluents, in which case the main concerns are homogeneity, segregation during transport and chemical stability.

Each of the Type A, Type B and Type C medicated articles and feeds of the present invention are prepared using art recognized conventional mixers, hammer mills, roller mills, pellet mills or extruders, associated manufacturing equipment and techniques associated with preparing formulations of the present invention. This equipment is all commercially available.

There are several forms of fish feed, including wet, moist, steam-pelleted and extruded dry pellets. However, two basic types of formulated feed are generally used in intensive fish culture: dry and semi-moist diets. The diets are similar, the basic difference being that semi-moist pellets contain a larger proportion of raw fish and by-products which contribute a higher moisture level to the final product. Moist feeds have some merit in coastal regions where fresh raw fish and by-products are regularly available and economical. It is also possible that the physical characteristics of moist pellets are more palatable to some fish species. However, there is no evidence that such feeds are nutritionally superior to dry feeds. Moist feed may contain pathogens since the feed ingredients are only submitted to moderate heat treatment (pasteurization). In contrast to moist diets, dry feed are heat-treated and generally free from pathogens. They are also easier to transport and store. The bulk purchase and storage of quality dry ingredients is possible and ensures a continuous supply of quality feed. The dry ingredients on the commodity market are more quality defined than raw fisheries products and can be supplied regularly. Hence it is possible to formulate dry feeds more precisely with the available knowledge of fish nutrition. Most nutrient in dry feeds are stable are room temperature and therefore dry feeds can be stored safely without freezing for periods which depend on storage conditions (approximately 3 months in a cool, shady, and well-ventilated location). Widely used dry feeds today may divide into three types: (1) steam-pelleted feed; (2) partially extruded, slow-sinking pellets, and (3) expanded and floating pellets. Feeding dry pellets either by hand or with automatic feeders is much simpler than that of moist feeds. The problem of acceptability of dry feeds by some fish species can usually be solved by better feeding techniques and fish culture management. Otherwise, fry which have difficulty in accepting dry feeds can be started with semi-moist feed and gradually shifted over the dry feed within 3-5 weeks. A formulated dry fish feed must be pelleted and/or crumbled so as to be durable and water stable. Formulated feeds must also have desirable physical and textural characteristics, and be of the correct sizes to be readily acceptable by different sizes of fish. Disintegrated and uneaten feed pollutes the water and creates stresses from low oxygen and high nitrogen and organic wastes, with serious effects on growth and health. Some of the important factors in manufacturing a durable, dry fish feed without fines are (1) physical properties of the ingredients, (2) particle size of ingredients, (3) conditioning time and temperature in the pellet mill, (4) quality of steam supply, (5) compression pressure through the die, and (6) efficiency of sifting/grading and fat-spraying equipment.

Fishfeeds are generally manufactured to a formula specific for the aquatic target species being fed and intended aquatic production system.

While most temperate freshwater diets may be largely based upon the use of plant protein and energy sources, and cold water marine diets are largely based upon the use of fishmeal and other fishery by-products, there can be regional differences which reflect optimal use of locally available and/or least-cost formulation of ingredients.

In most existing feed mills the coarse grains and possibly other ingredients will be ground in a hammer mill, roller mill or otherwise prepared by appropriate means to allow uniform mixing of the ingredients to formula specifications and further processing by pellet mill or extrusion to the cooled and finished product. The feed, properly cooled and dried after processing, is then ready for sacking or bulk delivery to the farm.

In aquaculture feeds particle sizes are typically smaller, some as small as 50 microns to allow proper mixing, pelleting or extrusion of the feed.

An important factor is the conditioning and cooking process of the mash, whether it is to be pelleted or extruded (or a system which employs the principles of both), the starch must gelatinize so that the feed is digestible and maintains its integrity in water. This will assure that the feed nutrients are consumed by the animal and do not end up as fertilizer or potential pollutant within the aquatic production system.

Generally, pelleting is less expensive than extrusion and may be cost-effective depending upon a variety of factors including the type and behavior of the species being cultured, types of ingredients available, and resources of the feed miller.

Generally, substances that may be included in fish feed and feedstuffs include fish meal, fish silage (hydrolysed fish), plant carbohydrate (such as wheat meal, corn meal, soy meal, etc.), fish oil, plant oil, colouring agents, vitamins, minerals, pharmaceuticals (such as antibiotics, growth promoters, etc), and plant proteins, especially storage proteins including gluten.

These additional substances may serve to provide a balanced diet for the fish fed with the nutritional composition; they may serve to adjust the lipid/protein balance, fish or plant oils may be used to increase lipid content; they may, like the colouring agents, be used to make the flesh of farmed fish more closely resemble that of wild fish, which is particularly desirable for farmed salmon; or they may serve to improve or protect the health of the creature receiving the feed, such as where antibiotics are used. The use of plant storage proteins, in particular gluten, however is desirable as it improves the texture, physical strength and lipid retention ability of the product.

Thus with such additional substances included, the product is a complete feed, especially a feed in pellet form or a feed or feedstuff in granular form (such as in powder, grain or meal form) comprising 1 to 2500 mg of spinosyn or a physiologically acceptable derivative or salt thereof per kg of feed or feedstuff.

Typically the protein content will be 30 to 60% by weight, preferably 35 to 58%, more preferably 40 to 55% on a dry weight.

The product will preferably have a lipid content of 8 to 35% by weight on a dry weight basis, more preferably 10 to 30%.

Vitamins, colouring agents, pharmaceuticals and minerals will generally form only a minor portion of the product, such as up to 10% by weight on a dry solids basis. Appropriate amounts can readily be calculated from the appropriate dosages and feed consumption rates for the fish receiving the feed.

Carbohydrates, such as digestible plant starch, for example wheat starch, will generally constitute up to 20% by weight on a dry weight basis of the product, preferably 5 to 15%.

The water content of the feed will be 0.5 to 10% for a dry feed, preferably 2 to 9% and more particularly 3 to 8%. For a wet feed, the water content will be greater than 10% to 70%.

The present invention further contemplates a solid feed comprising a formulation of the present invention containing spinosyn or a physiologically acceptable derivative or salt thereof, and fish feed which may be administered to fish or diluted with fish feed matter to afford a complete feed composition.

The amount of spinosyn or physiologically acceptable derivative or salt to be employed will vary with the specific improvement desired, the fish species, the age of the fish, and other factors known to those in the field of aquaculture. In general, a concentration in or on the fish feed of from 1 to 2500 mg per kg of fish feed will provide good results. In many instances, concentrations in the range of 75-2250 mg per kg will suffice.

The invention is illustrated by the following examples.

EXPERIMENT 1

Spinosad for the Treatment of Sea Lice Infestations of Atlantic Salmon

To determine the efficacy of Spinosad for the treatment of experimentally induced salmon louse (Lepeophtherius salmonis) infestations of Atlantic salmon (Salmo salar).

Fish will be acclimated to a recirculation system and artificially infested with sea lice. Spinosad will be administered, at varying dose levels, to groups of fish via top coated feed. The fish will be held for a period of 24 days post challenge and examined to determine level of infestation. A determination of the efficacy of Spinosad at varying doses will be made and a cost/benefit analysis conducted.

Spinosad will be incorporated into, or top-dressed onto, standard Atlantic salmon aquaculture production diets at zero and three inclusion rates of 250 mg, 750 mg and 2250 mg/kg of diet to produce the experimental diets (4×2 study design with 30 Atlantic salmon per experimental unit). All test fish will be uniquely identified, weighed and measured prior to initiation of the study. The entire population of test Atlantic salmon (est., 150 to 300 g body weight) will be infested with L. salmonis by a laboratory challenge model. Following secure attachment of the parasites, the infested Atlantic salmon will be transferred to individual experimental unit holding tanks and fed the designated experimental diet for the prescribed duration of 7 days. The diets will be coded and diet composition will be blinded to all research personnel on the study. Approximately 24 days post-challenge, salmon will be euthanized by an anaesthetic overdose, sea lice counted, collected and preserved in fixative, for recount, and the body weights and lengths of the salmon measured. Sea lice counts will be analysed to determine the efficacy of the treatment regimens and weight gains will be analysed for indication of impact of the treatment regimes on growth of the salmon.

TABLE 1

Average Weight Increase by Fed Spinosad for 4 Weeks and For an Additional 2 Weeks

| Dietary Spinosad (mg/kg) | Fish Weight (g) | Percentage Weight Increase |
|---|---|---|
| 0 | | |
| 250 | | |
| 750 | | |
| 2250 | | |

Formulation 1
Composition of Basal Diet for Channel Catfish

| Item | Amount |
|---|---|
| Ingredient (g/100 g): | |
| Menhaden fish meal | 12.0 |
| Dehulled soybean meal | 53.5 |
| Wheat midlings | 10.0 |
| Corn | 21.2 |
| Dicalcium phosphate | 1.0 |
| Trace mineral premix[1] | 0.1 |
| Vitamin premix[2] | 0.2 |
| Menhaden oil | 2.5 |

Formulation 1
Composition of Basal Diet for Channel Catfish

| Item | Amount |
|---|---|
| Nutrient: | |
| Crude protein (%) | 36.2 |
| Crude fat (%) | 5.7 |
| Digestible energy (kcal/g) | 3.2 |
| P/E (mg protein/kcal DE) | 11 |

[1]Trace mineral mix was the same as described by Reis, et al. [(1989). Protein-to-energy ratios in production diets and growth and body composition to channel catfish. Aquaculture, 77: 21-27] and provided the following (mg/kg of diet): Zn, 150; Fe, 44; Mn, 25; I, 5; Cu, 3; Se, 0.25.
[2]Vitamin premix provided the following (mg/kg diet): thiamin, 20; choline chloride, 2,000; niacin, 150; riboflavin, 20; pyridoxine, 20; folic acid, 5; calcium pantothenate, 200; cyanocobalamin, 0.06; retinol as (retinyl acetate) 4,000; all-rac-alpha-tocopherol, 50; cholecalciferol (1,000,000 IU/g), 2; menadione, 10; biotin, 1; L-ascorbic acid, 100; ethoxyquin (an antioxidant), 200.

Formulation 2
Composition of Semimoist Pellet for Chinook Salmon

| Ingredient | (%) |
|---|---|
| Anchovy meal | 55 |
| Condensed hydrolyzed fish[a] | 20 |
| Wheat middlings | 14 |
| Whey | 2 |
| Krill meal | 3 |
| Choline chloride | 1 |
| Vitamin mix[b] | 2 |
| Mineral mix[c] | 1 |
| Carboxymethylcellulose | 0.5 |
| Guar gum | 0.5 |

[a]Processing waste and by-catch.
[b]Each kilogram of premix supplied the following: vitamin E 15,200 IU; biotin 158 mg; vitamin B12 4 mg; folic acid 2200 mg; inositol 52,800 mg; menadione 1220 mg; niacin 29,500 mg; D-pantothenic acid 14,100 mg; pyridoxine 4100 mg; riboflavin 7040 mg; thiamin 5720 mg.
[c]Supplied the following as mg kg$^{-1}$ premix (I, 1000; Mn, 10,500; Zn, 7450; Cu 1550; Se, 160).

Formulation 3
Floating Pellet Composition for Atlantic Salmon

| Ingredients (g kg$^{-1}$) | |
|---|---|
| Norwegian herring meal[a] | 480 |
| Soybean meal | 220 |
| Gelatinized starch (wheat) | 210 |
| Fish oil | 50 |
| Vitamin mix | 20 |
| Mineral mix | 10 |
| Na-alginate | 10 |
| Chemical composition | |
| Moisture (%) | 9.1 |
| Protein (N × 6.25) (% DM) | 47.2 |
| Fat (% DM) | 10.7 |
| Gross energy (kJ g$^{-1}$ DM) | 20.7 |
| Digestible composition | |
| Digestible protein (% DM) | 43.9 |
| Digestible energy (kJ g$^{-1}$ DM) | 18.5 |
| Digestible protein/digestible energy ratio (mg kJ$^{-1}$) | 23.7 |

[a]70% crude protein.
DM, dry matter.

| Formulation 4 Floating Pellet Composition for Nile Tilapia ||
| --- | --- |
| Ingredients | (%) |
| Fish meal | 10 |
| Soy bean cake | 30 |
| Rapeseed cake | 25 |
| Wheat | 26 |
| Vitamin premix[a] | 1 |
| Vitamin premix[b] | 5 |
| Vegetable oil | 2 |
| Dry matter | 92.3 |
| % dry matter | |
| Crude protein | 35.6 |
| Crude lipid | 2.1 |
| Ash | 11.2 |
| Fibre | 6.6 |
| Gross energy (kJ/g) | 17.6 |

[a]Vitamin premix (mg/kg): thiamin, 10; riboflavin, 20; pyridoxine, 10; cobalamin, 2; retinol, 4; cholecalciferol, 0.4; phylloquinone, 80; folic acid, 5; calcium patotheniate, 40; inositol, 400; niacin, 150; tocopherol, 60; wheat powder, 218.6; chorine, 6000; ascorbic acid, 500.
[b]Mineral premix (g/kg): NaCl, 0.25; MgSO$_4$, 3.75; KH$_2$PO$_4$, 8; Ca(H$_2$PO$_4$), 5; FeSO$_4$, 0.72, (CH$_2$CHCOO)$_2$Ca•5H$_2$O, 0.88; ZnSO$_4$•7H$_2$O, 0.088; MnSO$_4$•4H$_2$O, 0.040; CuSO$_4$•5H$_2$O, 0.008; CoCl$_2$•6H$_2$O, 0.00025; KIO$_3$6H$_2$O, 0.00075; wheat powder, 0.112.

| Formulations 5-8 Compositions of Floating Pellets for Salmonids ||||
| --- | --- | --- | --- | --- |
| | 5 | 6 | 7 | 8 |
| Ingredients | | | | |
| Fish meal, herring | 20 | 35 | 18 | 18 |
| Blood meal, spray-dried | 9 | 9 | — | — |
| Corn gluten meal | 17 | 15 | 49 | 37.6 |
| Soybean meal | 12 | 14 | — | — |
| Poultry meal | — | — | — | 13 |
| Brewer's dried yeast | — | — | 6 | — |
| Wheat middlings | 20 | — | — | — |
| Whey | 8 | 10 | 11 | 9 |
| Vitamin premix | 0.5 | 0.5 | 1 | 0.5 |
| Mineral premix | 0.5 | 0.5 | 1 | 0.5 |
| L-Lysine | — | — | — | 1.4 |
| Fish oil | 13 | 16 | 14 | 20 |
| Digestible Composition | | | | |
| Digestible protein, % | 37 | 44 | 44 | 42 |
| Digestible energy, MJ/kg | 17 | 20 | 20 | 21 |

We claim:

1. A method of controlling sea lice in aquaculture raised fish comprising administering an effective amount of spinosad or salt thereof to aquaculture raised fish.

2. The method of claim 1 wherein the fish is a catfish.

3. The method of claim 1 wherein the fish is a carp.

4. The method of claim 1 wherein the fish is a salmon.

5. The method of claim 1 wherein the fish is a trout.

6. The method of claim 1 wherein the fish is a yellowtail.

7. The method of claim 1 wherein the fish is a striped bass.

8. A method of improving production of aquaculture raised fish which comprises administering to the fish a nutritionally balanced fish feed comprising 1-2500 mg of spinosad or salt thereof per kg of fish feed.

9. The method of claim 8 employing a fish feed comprising 75-2250 mg/kg of spinosad or salt thereof.

10. The method of claim 9 wherein the fish is a catfish.

11. The method of claim 9 wherein the fish is a carp.

12. The method of claim 9 wherein the fish is a salmon.

13. The method of claim 9 wherein the fish is a trout.

14. The method of claim 9 wherein the fish is a yellowtail.

15. The method of claim 9 wherein the fish is a striped bass.

16. A solid, aquaculture raised fish feed formulation comprising 75 to 2250 mg of spinosad or salt thereof per kg of fish feed.

* * * * *